US009475339B2

(12) United States Patent
Anuradha

(10) Patent No.: US 9,475,339 B2
(45) Date of Patent: Oct. 25, 2016

(54) PROCESS OF FLORAL BOTANICAL COLLAGE DECOUPAGE

(76) Inventor: Sahu Anuradha, Chhattisgarh (IN)

( * ) Notice: Subject to any disclaimer, the term of this patent is extended or adjusted under 35 U.S.C. 154(b) by 618 days.

(21) Appl. No.: 14/000,229

(22) PCT Filed: Apr. 25, 2011

(86) PCT No.: PCT/IN2011/000268
§ 371 (c)(1),
(2), (4) Date: Aug. 19, 2013

(87) PCT Pub. No.: WO2012/120523
PCT Pub. Date: Sep. 13, 2012

(65) Prior Publication Data
US 2013/0337418 A1    Dec. 19, 2013

(30) Foreign Application Priority Data

Mar. 9, 2011  (IN) .............................. 303/KOL/2011

(51) Int. Cl.
*B44C 5/06*     (2006.01)
*A01N 3/00*    (2006.01)
(52) U.S. Cl.
CPC .. *B44C 5/06* (2013.01); *A01N 3/00* (2013.01)
(58) Field of Classification Search
USPC .......................................................... 434/93
See application file for complete search history.

(56) References Cited

U.S. PATENT DOCUMENTS 3,718,529 A * 2/1973 Coleman ................... B44C 5/06
                                                              156/57
5,656,343 A * 8/1997 Baker ....................... A01N 3/00
                                                              156/57

FOREIGN PATENT DOCUMENTS

| CN | 1268451 A | 10/2000 |
|---|---|---|
| JP | 2005-255620 A | 9/2005 |
| JP | 2007-332038 A | 12/2007 |

* cited by examiner

*Primary Examiner* — James Hull
(74) *Attorney, Agent, or Firm* — Fraser Clemens Martin & Miller LLC; William J. Clemens

(57) ABSTRACT

A process for dry flower craft includes cutting craft media (dry botanicals with stencils) and mounting the same on any surface or product in combination with other botanical elements like bamboo, grass, weeds, seed, stem, tendrils, fiber, sola wood in any desired manner including an artistic manner. The process includes reducing color loss while drying and storage of vegetation and also during crafting of the vegetation, making stencils of cheapest materials such as cardboard and paper, cutting out motifs, shaping petals in any desired shape, and pasting the same with known adhesives. The botanicals are dried prior to floral collage decoupage by drying while using a mixture of desiccant of silica gel+silversand+non iodized salts (1:1:1 ratio). Finally obtaining floral decoupage or only floral collage or a combination of both in design processing as application of the craft, by making the floral resin laminates by reducing the peroxide harder by 1%.

11 Claims, 2 Drawing Sheets

PROCESS OF FLORAL BOTANICAL COLLAGE DECOUPAGE

FIELD OF INVENTION

The present invention relates to an improved process for floral botanical collage decoupage.

BACKGROUND OF THE INVENTION

In the earlier art, a process for preparing/decorating an object with pressed dried flowers was already known.

The said known process consists of mounting of dry flowers in an artistic manner or any other desired manner on any object mostly paper.

The said known process has certain disadvantages which are given below:
1. Color texture, shape, smooth contour of dried vegetation obtained were of very poor quality.
2. Additionally seeds, weeds, grass, bamboo, tendrils, Sola wood, Natural fibers and other dry botanicals elements which are essential to reduce the cost and induce better design with utility of botanicals of variable source to complete the definition of collage were not used.
3. The obtained product is very poor in hand craft technical aspect and of poor design, and therefore does not appeal to customers.
4. Use of Stencils to cut the botanicals was not used ever, hence decoupage of botanicals is a new invention.
5. Botanical decoupage and collage not in existence.
6. Technique of drying and pressing of botanicals not used which can remove the disadvantages towards color retention and texture for longer period for dried botanicals almost 4 times.

SUMMARY OF THE INVENTION

According to present invention it has been surprisingly found that use of mixture of desiccant silica gel+silversand+non iodized salts is a crux of the present invention.

Both the drying technique & craft technology along with the concept of Floral collage decoupage is a new invention against pressed dry flower craft as known prior art.

Floral Resin laminate is an invention.

Thus by adopting the process of floral resin lamination in the present invention we stop the further deterioration by arresting oxidation of color pigments as the dried botanical are permanently embedded in hardened resin, hence no excess of atmospheric air for it.

Wherein dried and pressed flowers or botanicals are hand crafted on any surface, such as on paper, with the help of a stencil to create floral decoupage and without use of stencils but with combination of other botanicals like bamboo, grass, weeds, seeds, stem, tendrils, fiber, solawood to create floral collage. The color, texture and shape of dried botanicals are of superior quality and more stable for a longer period. The floral handicraft created by above improved process of Floral collage decoupage is not of poor quality and appeals better to the eye.

These and other objects have been obtained by the process of the present invention.

According to the present invention there is provided an improved process for floral collage decoupage—(an improved process of pressed dry flower craft) which comprises:
(i) cutting craft media (dry botanicals) by hand with card paper stencils and mounting the same on any surface of product with combination of other botanical elements like bamboo, grass, weeds, seeds, stem, tendrils, fiber, Sola wood in any desired manner including artistic manner; along with better drying and pressing technology which comprises reducing the oxidation and isomerization of carotenoid and Anthocyanin and hence reducing color loss while drying and storage of vegetation and also during crafting of the vegetation;
(ii) making stencil of cheapest material such as cardboard and paper, and hand cutting to make cutouts (motif);
(iii) shaping the petals in any desired shaped and synchronized pasting the same with known low pH alkaline adhesives; characterized is that botanicals are dried prior to floral collage decoupage by electric oven or microwave oven drying with the use of mixture of desiccant silica gel+silversand+non iodized salts. (1:1:1 ratio)

Method for drying flowers involves covering botanicals with something that draws moisture out, generally referred to as a desiccant.

The drying is enhanced to reduce time to about one to two hours instead of 3 days for conventional electric oven and dried in silica gel desiccant mixture, in microven for less than 24 hours and storing the same under in a cold, dry and dark place in a vacuum suctioned container.

The organic manure contains nitrogen, phosphorous and potassium as nutrients to give a 20% low pH in uniform relative availability to the (bio-physiological system and) structured component of the plant for color stability and vegetation in dried botanicals, which is most important for floral collage decoupage.

The said organic manure is used to reduce 20% acidity of plant structure & its bio-physiological system and thereby reducing the senescence process that is an aging process to obtain best natural colored texture and hence dried vegetation grown in organic manure are better in texture and color and more stable for longer duration to form dried botanicals as craft ingredients of almost 4 times better.

The above conditions reduces the oxidation and isomerization of carotenoid and Anthocyanin and other color pigments and hence reduced color loss while drying and storage of vegetation and also during crafting of the vegetation.

During storage exclusive of oxygen, light and humidity is facilitated to stop decomposition of dried botanicals and crafted product. Hence vacuum storage in dark, dry and cool place is most important.

Three different pigments—chlorophyll, flavonoids, and carotenoids—are mixed in different proportions, to give color and shade to flowers.

Flavonoids are divided into two groups—pigmented anthocyanins and colorless copigments.
(i) Anthocyanin pigments take their color from the range of red, purple, or blue, depending on their pH. Anthocyanins are partly responsible for the red and purple colors.
(ii) The carotenoids impart yellow, purple and orange colors. There are 300 types of carotenoids of which mains one are lycopene, b-carotene and a-tocopherol.

Among three, chlorophyll has a more stable molecular structure compared to Anthocyanin and Carotenoids.

And among two, Carotenoids have still more sensitive in structure stability.

Color changes depend upon the interplay of isomerization and oxidation.

The main causes of color degradation of dried botanicals during processing are isomerization and oxidation (enzymatic and non enzymatic).

This can be influenced by many factors.

The presence of humidity accelerates destruction of all type of color pigments present in all vegetation in natural form.

Both b-carotene and a-tocopherol are destroyed by oxidation. This reaction is accelerated by ultraviolet light and heat, and becomes a photochemical process.

The destruction of b-carotene in forages is first an enzymatic process and is due to a lipoxygenase system. Lipoxygenases, a group of isoenzymes, are present at varying levels in a wide number of species of plants. Enzymatic destruction of carotene begins when the forage (vegetation) is chopped or heated while cooking or drying. Increased chopping and grinding also accelerates enzymatic destruction, as does raising ambient temperature and humidity.

During drying, the losses of b-carotene and a-tocopherol can equally be due to isomerization and oxidation.

Degradation Because of Isomerization of Carotenoids

As a consequence, the two isomers cis & trans demonstrate substantial variations of their thermodynamic and kinetic constants and also color properties. A possible explanation for these characteristics is presented, making use of molecular modelling and taking into account the three-dimensional structures of the pigments.

DETAILED DESCRIPTION OF THE INVENTION

Figure 1:
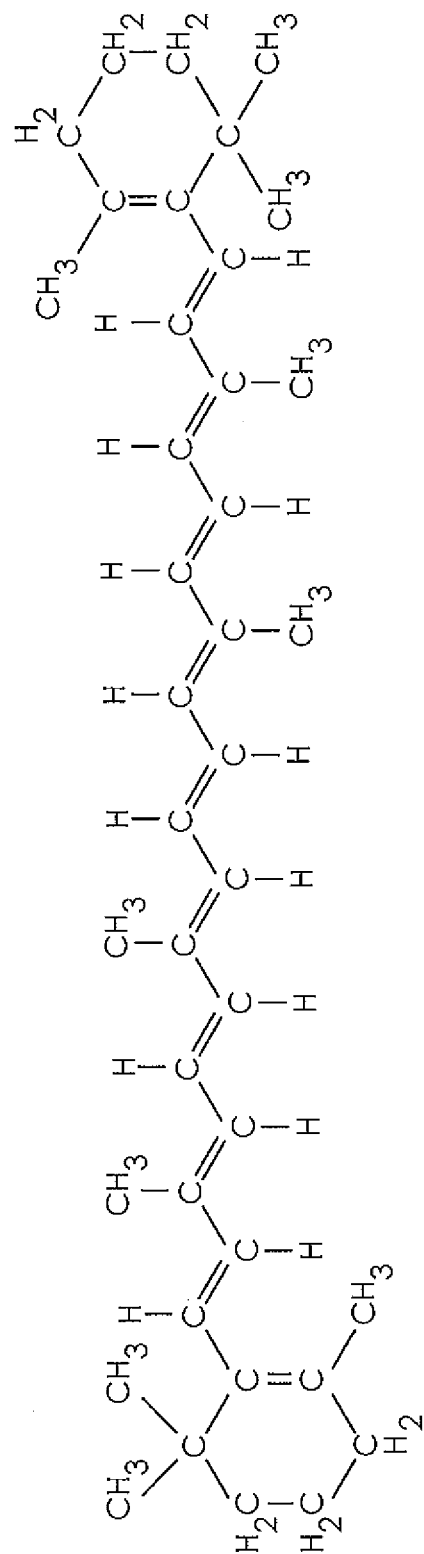
FIG. 1 shows the chemical structure of beta-carotene.

The FIG. 1 shows the structure of beta-carotene, one of the most abundant carotenoids. The system of alternating single and double bonds that is in this molecule runs along the hydrocarbon chain that connects the two benzene rings. The electrons of the double bonds actually migrate though the chain and also make this molecule an efficient absorber of light. The long system of alternating double and single bonds constitutes a conjugated system in which the $\pi$ electrons are effectively delocalized over the entire length of the polyene chain. This feature is responsible for the molecular shape, chemical reactivity and light absorbing properties, and hence color of carotenoids (Britton, 1995). At least seven conjugated double bonds are needed for the carotenoid to impart color. Each double bond in the polyene chain of a carotenoid can exist in two configurations, trans or cisgeometrical isomers. Most carotenoids occur in nature predominantly or entirely in the all trans form (stable).

The polyene chain is the cause of instability of carotenoids including their susceptibility to oxidation and geometric isomerization.

Heat, light and acids promote isomerization of trans-carotenoids to the cis-form Beta-carotene. The conjugated system in which the $\pi$ electrons are delocalized over the entire length of the polyene chain is responsible for the molecular shape, chemical and physical reactivity and the antioxidant properties of carotenoids. It is sensitive to heat, light, alkaline pH value, oxygen and duration of drying process.

Isomerization converts all-trans isomers to cis-isomers due to additional energy input and results in an unstable, energy-rich station. Heat induces isomerization of the all-trans to cis forms. The cis-isomers increase with temperature and processing time. A significant increase in the cis-isomers with a simultaneous decrease in the all-trans isomers can be observed in dehydrating botanicals samples using the different dehydration methods. Subsequent isomerization of Carotenoids leads to significant increase in the cis-isomers with a simultaneous decrease in the all-trans isomers and hence into structural fragmentation results in a series of low molecular weight compounds which leads to decoloration of dried botanicals. During drying, the losses of b-carotene and a-tocopherol can equally be due to isomerization. Due to the structural configuration of these products, the removal of moisture must be accomplished in a manner that will be least deteriorating to the product's color quality.

In general, dehydrated Botanicals have poor lycopene stability also and hence they have to be carefully processed and promptly placed in a hermetically sealed containers and in inert & vacuum atmosphere for storage. Isomerization leads to decolorization or fading of colors in decayed and dried botanicals.

Oxidation of Carotenoids and Degradation of Color

The Second major cause of loss of carotenoid is enzymatic and non enzymatic oxidation, which is dependent on availability of oxygen and structure of Carotenoid.

This is the reason for decolorization or decomposition which gives brown color to decomposed dried botanicals.

Loss of color or browning (decomposition) in dried vegetation is result of structural fragmentation of carotenoid. Subsequent fragmentation results in a series of unstable low molecular weight compounds which leads to color decay as at least seven conjugated double bonds are needed for the carotenoid in its structure to impart color.

Chemical oxidation of carotenoid is non enzymatic Oxidation, causing oxidative rancidity, loss of color leading to Maillard reaction, causing discolorization and change in texture. Here Reaction between carbony and amino groups leads to formation of intermediates known as Phenolic compounds or Melanoidins which leads to browning of color pigments which is non enzymatic. Hence dried botanicals darkens on exposure to air as a result of conversion of phenolic compounds to brown melanoidins with foul smell. It is generally accepted that the initial stage of oxidation involves epoxidation and formation of apocarotenoids.

Oxidation of Carotenoids leads to formation of epoxy carotenoids, apocarotenoids and hydroxy carotenoids which are Glycosylamines and Amadori products and are unstable low molecular structure leading to structural fragmentation. Glycosylamines and Amadori products are unstable intermediates formed during the course of the Maillard reaction.

The concentration of the intermediates depends upon the reaction conditions (pH, temperature and time). Low pH, low temp and lesser time is favorable, as it leads to lesser quantity of these intermediates.

In the pH range 4-7, Amadori products undergo further degradation to give 1- and 3-deoxydicarbonyl compounds. The % open chain form and rate of mutarotation increases with Temperature and pH.

Acidic or high pH influences the ratio of intermediate unstable products formation.

The rate of brown color (decay) formation can be reduced by decreasing the pH.

Enzyme oxidation of carotenoid is because of Polyphenoloxidase, causing enzymic browning. Enzyme Lipoxygenase, causes oxidative rancidity. Enzyme Lipase, causes lipolytic rancidity. Enzyme Protease, causes gelation, flavor, foul smell and brown color texture change.

This is enhanced by presence of atmospheric humidity/oxygen, high pH value or acidic conditions and variation in temperature.

Both the process leads to browning of dried vegetation and rancid foul smell from it, if proper storage is not implemented.

Hence low temperature, low pH, dark and vacuum storage condition is very important for keeping dried botanical and finished crafted elements for prolonged storage.

There is two type of color degradation firstly fading of colors because of isomerization and secondly oxidation both enzymatic and non enzymatic leading to browning of color & texture along with decay and foul smell in dried vegetation.

Hence technical improvement in the present technology with reasons for Drying and pressing of dried botanicals are as follows:

1. Salt treatment reduces the humidity of vegetation by absorption (in desiccant mix with silica gel), reduce carotenoid degradation, because it facilitates fast drying in lesser time at low temperature of 45 to 47 degrees.
2. Minimum oxygen exposure to avoid oxidation of carotenoid is important, hence vacuum storage, in cool temperature and non humid condition is most important for raw material preservation.
3. Low temperature and quick drying between 45 to 47 degrees is best for color retention.
4. Low pH for glue, blotting paper for drying and storage condition is most important.
5. Dark condition while drying and storage is most important as photochemical process in presence of light and oxygen leads to degradation in structure of carotenoids and hence loss of color. All the color pigment of cartenoid and Anthocyanin has light absorbing property as it plays an active role in Photosynthesis along with chlorophyll in presence of sunlight.
6. Organically grown vegetation which has 20% less acidity in its biophysiological system and structure of the plant.

This is the second portion of the claim towards the technological crafting methodology of floral collage decoupage with improved craft ingredients of colorful and good textured dried botanicals obtained by present dried and pressed process.

Decoupage is the technique of decorating a surface with pasting of cutouts. Collage is an artistic composition of variable materials and objects pasted over a surface, often with underlying lines and color of different botanical origins.

We can have only floral decoupage or only floral collage or as third option a combination of both in design processing as application of the craft.

Floral Decoupage:

Floral Decoupage is the art of cutting (with stencils) a craft media (dry botanicals) and mounting it on any surface or product as object and when with a combination of other special botanical elements like bamboo, grass, weeds, seeds, stem, tendrils, fiber, sola wood, Etc. it formulates into floral collage.

For the very first time we are coming up with floral collage decoupage.

Here we are cutting (as cutouts) dried pressed floral petals, leaves, sola wood, leaf skeleton, Natural fibers and mounting them in an artistic combinations and along with bamboo, grass, weeds, tendrils, seeds, stem and other botanicals in dried form as special effect to make a collage and both in combination forms floral collage decoupage.

The main technique in craft of floral decoupage is nothing more than stencil cutting and pasting of dried botanicals in an artistic manner.

Decoupage is the arrangement of cutouts and pasting on the surface or object of handmade paper, wood, fiberglass and used to creative decoration. Collage is an artistic composition of variable materials and objects pasted over a surface, often with underlying lines and color of different botanical origins.

We use stencil to make repeated similar cutouts of dried botanicals specially petals, leaves, Natural fibers, Solawood, Leaf skeleton, etc.

The cheapest material is card board hard paper, but if you're going to use the stencil several times, make sure original drawing is duplicated as multiple stencil, as after a few uses, it will probably become damaged and no longer capable of reproducing exactly the same design.

Below is the process to make the stencil.

Draw or trace a design onto your sheet (card board paper). Then, cut out the inside carefully with a new craft scissor, or blade.

Tools needed to create the shapes used in decoupage projects include a pair of sharp, pointed scissors. Often the curved tips of nail scissors, along with their sharpness, are selected for intricate work. Good light and good vision are also needed to precisely cut the shapes without distortion or loss of shape and details.

Cut out motifs & Shape the Petals in the form of drop, heart, spindle, oval, circular or any other desirable shape as accurately as possible. Twigs, leaves, tendrils and other natural items are often important additions to the equation, too.

When doing the actual cutting of dried botanicals (flowers & leaves) the scissors should be tilted somewhat towards the right to obtain a slightly better edge. Scissors, razor blades or stencil knives, all sharp cutting tools, should be held at a slanted angle as you cut.

Pasting is important because the even application of an adhesive will ensure the item will lie flat, without bubbles or puckers. Ideally, the cutout would be placed reversed on a sheet of clean paper or plastic and the adhesive lightly applied with needle over the entire reversed surface. Every point, tip and edge should be covered so that it will lie down perfectly. Play with the positions of the images so you get a desired look at the end when the entire pasting is done.

Tool for pasting and placement of botanicals on the surface is six inch long needle holding it like pen in the right hand.

Paste the glued cut out botanicals on the surface to recreate the desired floral patterns.

Trim cut all individual petals before attaching them as the flower . . . one petal at a time.

Cut dry flower petals each individually and paste petals joined from the center into desired patterns of flowers. Bamboo, Twigs, leaves and other natural items are often important additions to the equation, to make phenomenon of Botanical collage.

It is very important to use a neutral pH resin glue for pasting of flowers to avoid decoloration of dried botanicals at any stage of crafting.

Floral Collage

Same technique of pasting is used in this case but cutting of petals or flowers are not required and they are used as in its original shape and size. (stencils are not required). Then they are technically a floral collage. Just slight trimming or adjustments are required not reshaping. In addition seeds, weeds, grass, bamboo, tendrils, and other dry botanicals elements are used.

A botanical collage, is defined where many different botanicals as ingredients may be combined to create a textural and visually interesting arrangement on a surface or object.

As there is versatility in the species of flowers regarding to shapes and colors. They not only look original but beautiful and graceful too.

By using process to present invention:

Floral laminates may be made on surface of glass, fiber glass, acrylic, wood, ceramics, and veneers, etc.

1) Work On flat surfaces (180°). Surface should be smooth, dry, clean and oil free.
2) Paste the dry flowers and other botanicals as directed in patterns or designs. On the surface Pasting should be very firm or else in resin it will tear off or get displaced to spoil the design in permanency.
3) Avoid making floral laminates in Rainy seasons, as results are not good.
4) Design the dry flowers by pasting them on surface with good finish.
5) With hair dryer, blow the surface of the laminate after flower pasting, in order to dry the surface, remove any unwanted particles, repaste the flowers and other elements in case any of them is not properly glued. (Repair)
6) Keep the floral laminates for one hour in direct sunlight, in order to remove last trace of moisture in flower, glue or of laminates itself.
7) Place the laminate floral with the stretched thick cellophane on top of it, about 4 inch oversized to the laminate to facilitate the procedure. Keep weight at four corners of the Cellophane so that the laminate is safe and dry up. Remove the cellophane and proceed.
8) Mix 2 g of hardener MEK (peroxide hardener) into the 200 g pre-mixed resin (epoxy resin), mix thoroughly. Blow away any bubbles that may have formed on the mixture. The bubbles should be removed or they will produce holes on the laminate. Resin is a clear polyester medium that mixes with hardeners together as a liquid and dries hard and clear.

The resin used is preaccelerated polyester resin dissolved in styrene monomer. The polymerization is completed with the addition of hardener to the resin, either acetylacetone peroxide or methyl ethyl. The amount of hardener needed is 1% to Resin.

For floral laminates only one percent is add to preserve the color of the flowers as if more than one percent is added it generates heat during the lamination process while reacting with resin chemically, leading to fading of floral colors. (due to heat generation, isomerization of color pigments leads to decoloration of flowers) It will take few 3-4 extra hours in drying but with better results.

9) Pour the resin mixture in the center of the floral panel. Cover with cellophane.
10) Use squeegee with hand pressure and fast to spread the resin evenly and make sure no bubbles are present. Spreading should be from the center going out. Any air bubbles need to be removed before the coat dries up. Even pressure should be used to spread the resin and to compress. Allow to cure in 15-30 minutes.
11) Put equal weight on the corners of the laminate to ensure that the cellophane does not lift during the resin curing process. Leave Overnight until the resin sets completely. Usually, resin will set dry and cellophane will easily peel off after the laminate dries up. Trim the corner lines in case the resin has over flown the laminates to give good finish.

12) Once the resin dries, you will have a clear view of the dry flower, and the flower will not be able to decay, as it has no access to oxygen.
13) Work in a well-ventilated area. Wear a protective mask to prevent the inhalation of excess fumes from the epoxy resin. Put on rubber gloves to protect your skin from coming in contact with the resin. Open all the windows in the room and turn on a fan to exhaust air from the room. If you have a breathing mask, put it on. Resin is toxic, so the less you breathe in, the better.

Preservation of Dried Flowers as Floral Laminates with Clear Resin

The problem with saving dried flowers is that as the flower dries out, it becomes increasingly fragile and delicate, which makes handling or touching the flowers nearly impossible. This also means that displayed flowers become dusty over time, and they cannot be cleaned without destroying them. One solution is the floral laminates in polyresin. Flowers are one of life's greatest pleasures. Unfortunately, their lives are fleeting after they are cut. Through drying, it is possible to hold on to cut flowers for years. Dried flowers are quite long lasting, but like their fresh counterparts, they, too, are vulnerable to the passage of time. Their colors fade, and their leaves and petals crumble. By treating or embedding dried flowers (as laminates) in resin, however, it is possible to protect and preserve them even longer, and floral Laminates can be done on any surface of wood, veneer, fiber glass, acrylic, ceramics, bamboo, textiles or any natural surface.

Resin Floral Laminates:

We Mix 2 g of hardener MEK (peroxide hardener) into the 200 g pre-mixed resin (epoxy resin), usually in common method about 2% or little more of hardener is added to the resin mix. But it leads to good amount of heat generation in the chemical processing of it, which leads to decay of color.

We reduce the amount of hardener by 1%, allowing it to take comparatively extra few couple of hours to harden the transparent resin, but facilitating very less heat generation in the process to avoid isomerization of color pigments. Secondly the oxidation process is arrested in permanency because the flowers are forever embedded under the dried a resin hence no more access to oxygen.

Thus by resin lamination we reduce both isomerization and oxidation of color pigments and hence achieve better color retention of dried botanicals in resin laminated floral sheets.

Figure 2:
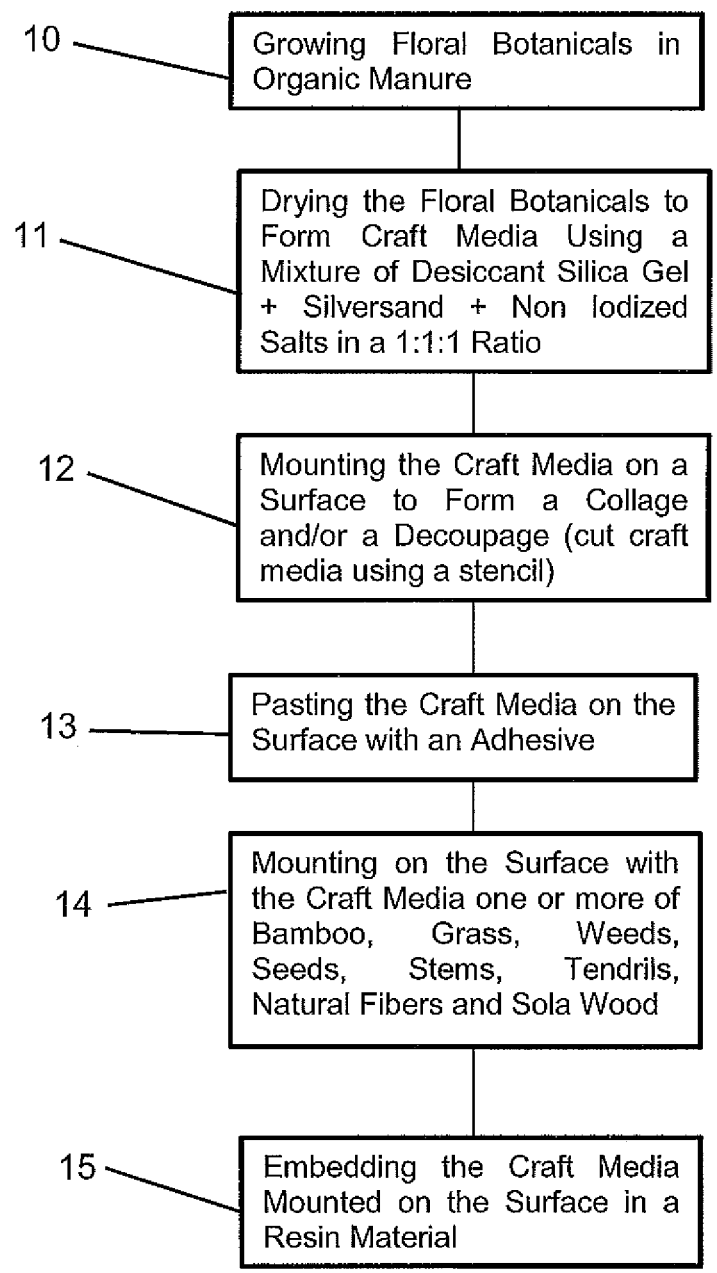
FIG. 2 is a flow diagram of the steps in the process for crafting floral botanicals into collage and/or decoupage according to the invention.

FIG. 2 is a flow diagram showing the basic steps of the above-described process for crafting floral botanicals into collage and/or decoupage comprising the steps of:

Step 10 growing the floral botanicals in organic manure containing nitrogen, phosphorous and potassium is used as a nutrient to produce a pH of 20% or lower to reduce a senescence process in the floral botanicals thereby providing color stability;

Step 11 drying floral botanicals to form craft media using a mixture of desiccant silica gel+silversand+non iodized salts in a 1:1:1 ratio;

Step 12 mounting the craft media formed in the Step 11 on a surface to form a collage and/or mounting cut craft media formed in the Step 11 on the surface to form a decoupage wherein the craft media is cut using at least one stencil if a decoupage is to be crafted;

Step 13 mounting by pasting the craft media on the surface with an adhesive;

Step 14 optionally mounting on the surface with the craft media one or more of bamboo, grass, weeds, seeds, stems, tendrils, natural fibers and sola wood; and Step 15 embedding the craft media mounted on the surface in a resin material.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A process for crafting floral botanicals into collage and/or decoupage comprising the steps of:
   (i) drying floral botanicals to form craft media using a mixture of desiccant silica gel+silversand+non iodized salts in a 1:1:1 ratio;
   (ii) cutting the craft media using at least one stencil if a decoupage is to be crafted;
   (iii) performing at least one of mounting the craft media formed in the step (i) on a surface to form a collage and mounting the cut craft media formed in the step (ii) on the surface to form a decoupage; and
   (iv) performing the step (iii) by pasting the craft media on the surface with an adhesive.

2. The process according to claim 1 including mounting on the surface with the craft media one or more of bamboo, grass, weeds, seeds, stems, tendrils, natural fibers and sola wood.

3. The process according to claim 1 including performing the step (i) in an oven for less than 24 hours and storing the dried craft media under vacuum.

4. The process according to claim 1 including growing the floral botanicals in organic manure containing nitrogen, phosphorous and potassium is used as a nutrient to produce a pH of 20% or lower to reduce a senescence process in the floral botanicals thereby providing color stability.

5. The process according to claim 1 including after the step (i) storing the craft media under vacuum exclusive of oxygen, light and humidity to reduce decomposition of the craft media.

6. The process according to claim 1 including embedding the craft media mounted on the surface in a resin material.

7. The process according to claim 6 including mixing 1% by weight of a hardener into a pre-mixed resin to reduce heat and avoid isomerization of color pigments in the craft media.

8. The process according to claim 1 including forming the stencil of cardboard or paper.

9. The process according to claim 1 including performing the step (ii) by shaping petals of the floral botanicals into at least one desired shape.

10. The process according to claim 1 including performing the step (iii) by mounting the craft media formed in the step (i) on a surface and mounting the cut craft media formed in the step (ii) on the surface to form a combination collage and decoupage.

11. A method for crafting floral botanical collage decoupage comprising the steps of:
    (i) drying floral botanicals to form craft media using a mixture of desiccant silica gel+silversand+non iodized salts in a 1:1:1 ratio and drying in an oven for less than 24 hours;
    (ii) cutting the craft media using at least one stencil if a decoupage is to be crafted;
    (iii) performing one of mounting the craft media formed in the step (i) on a surface to form a collage, mounting the cut craft media formed in the step (ii) on the surface to form a decoupage, and mounting on the surface both the craft media formed in the step (i) and the cut craft media formed in the step to form a combination collage and decoupage;
    (iv) performing the step (iii) by pasting the craft media on the surface with an adhesive; and
    (v) embedding the craft media mounted on the surface in a resin material.

\* \* \* \* \*